(12) United States Patent
Karime et al.

(10) Patent No.: US 9,944,582 B2
(45) Date of Patent: Apr. 17, 2018

(54) METHOD FOR THE PURIFICATION OF ACETIC ACID AND ACRYLIC ACID

(71) Applicant: SAUDI BASIC INDUSTRIES CORPORATION, Riyadh (SA)

(72) Inventors: Mustapha N. Karime, Riyadh (SA); Faisal Baksh, Manama (BH); Mubarik Bashir, Riyadh (SA); Zeeshan Nawaz, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/787,683

(22) PCT Filed: May 19, 2014

(86) PCT No.: PCT/US2014/038573
§ 371 (c)(1),
(2) Date: Oct. 28, 2015

(87) PCT Pub. No.: WO2014/189829
PCT Pub. Date: Nov. 27, 2014

(65) Prior Publication Data
US 2016/0075630 A1    Mar. 17, 2016

Related U.S. Application Data

(60) Provisional application No. 61/825,205, filed on May 20, 2013.

(51) Int. Cl.
| C07C 51/44 | (2006.01) |
| C07C 67/08 | (2006.01) |
| C07C 51/215 | (2006.01) |
| C07C 51/46 | (2006.01) |

(52) U.S. Cl.
CPC ............ *C07C 51/44* (2013.01); *C07C 51/215* (2013.01); *C07C 51/46* (2013.01); *C07C 67/08* (2013.01)

(58) Field of Classification Search
CPC .................................................... C07C 51/44
See application file for complete search history.

(56) References Cited

U.S. PATENT DOCUMENTS

| 2,748,159 A | 5/1956 | Finelli |
| 2,862,958 A | 12/1958 | Goreau |
| 3,433,831 A | 3/1969 | Yomiyama et al. |
| 3,459,736 A | 8/1969 | Dalibor |
| 3,666,632 A | 5/1972 | Honda et al. |
| 5,198,580 A | 3/1993 | Bartek et al. |
| 5,243,069 A * | 9/1993 | Emmons ............... C08F 20/28 526/260 |
| 5,785,821 A | 7/1998 | Sakamoto et al. |
| 5,880,310 A | 3/1999 | Ageishi et al. |
| 5,910,607 A | 6/1999 | Sakakura et al. |
| 6,160,162 A | 12/2000 | Karim et al. |
| 6,352,619 B1 * | 3/2002 | Fauconet ............... C07C 51/44 203/29 |
| 6,399,817 B1 | 6/2002 | Chapman et al. |
| 7,321,058 B2 * | 1/2008 | Machhammer ......... C07C 5/333 562/545 |
| 7,622,607 B2 | 11/2009 | Fauconet et al. |
| 2016/0096798 A1 | 4/2016 | Bashir et al. |

FOREIGN PATENT DOCUMENTS

| CN | 1270952 A | 10/2000 |
| CN | 1145527 C | 4/2004 |
| CN | 1625544 A | 6/2005 |
| CN | 1697818 A | 11/2005 |
| CN | 1835908 A | 9/2006 |
| CN | 1884249 A | 12/2006 |
| CN | 101269899 A | 9/2008 |
| CN | 101367720 A | 2/2009 |
| CN | 101530780 A | 9/2009 |
| EP | 0551111 A1 | 7/1993 |
| EP | 0861820 | 9/1998 |
| GB | 783463 | 9/1957 |
| GB | 813867 | 5/1959 |
| GB | 1058242 | 2/1967 |
| GB | 1182809 | 3/1970 |
| JP | S4620372 | 6/1971 |
| JP | S4634692 | 10/1971 |
| JP | S497216 A | 1/1974 |
| JP | S4995918 A | 9/1974 |
| JP | S4946942 B1 | 12/1974 |
| JP | S5011364 | 4/1975 |
| JP | 62267341 A | 11/1987 |
| JP | H0341051 A | 2/1991 |
| JP | H05246941 A | 9/1993 |
| JP | H0948744 A | 2/1997 |
| JP | H09151158 A | 6/1997 |
| JP | 09263566 A | 10/1997 |
| JP | H10306052 A | 11/1998 |
| JP | 2005179352 A | 7/2005 |
| JP | 2005232008 A | 9/2005 |
| JP | 2005320302 A | 11/2005 |
| JP | 3832868 B2 | 10/2006 |
| JP | 2006316066 A | 11/2006 |
| JP | 3937495 B2 | 6/2007 |
| JP | 4809532 B2 | 11/2011 |
| WO | 2005021482 A1 | 3/2005 |

OTHER PUBLICATIONS

International Search Report for PCT/US2014/038573 (KS30054PCT) mailed Nov. 13, 2014, 5 pages.
Written Opinion of the International Searching Authority for PCT/US2014/038573 (KS30054PCT) mailed Nov. 13, 2014, 6 pages.

(Continued)

*Primary Examiner* — Sudhakar Katakam
*Assistant Examiner* — Ana Z Muresan
(74) *Attorney, Agent, or Firm* — Cantor Colburn LLP

(57) ABSTRACT

The present disclosure relates to a method for purifying an acid, wherein the method comprises: a) producing a crude product mixture by a partial oxidation reaction, wherein the crude product mixture comprises acrylic acid and acetic acid; b) purifying the crude product mixture by distillation using a high-boiling solvent to purify the acrylic acid; and c) purifying the crude product mixture by distillation using a low-boiling solvent to purify the acetic acid.

25 Claims, 1 Drawing Sheet

(56) References Cited

OTHER PUBLICATIONS

Habib, Rowshanul and Karim, M. Rezaul, "Antimicrobial and Cytotoxic Activity of Di-(2-ethylhexyl) Phthalate and Anhydrosophoradiol-3-acetate Isolated from Calotropis gigantea (Linn.) Flower", Mycobiology (Mar. 2009);37(1): 31-36.
International Preliminary Report on Patentability, PCT/IB2014/061953, Issued Dec. 17, 2015.
International Preliminary Report on Patentability, PCT/US2014/038573, Issued Dec. 3, 2015.
International Search Report and Written Opinion, PCT/US2014/038573, issued Nov. 13, 2014.
International Search Report of the International Searching Authority for PCT/IB2014/061953 mailed Sep. 24, 2014, 5 pages.
International Search Report and Written Opinion, Mailed Sep. 24, 2014.
Sastry, V.M.V.S. and Rao, G.R.K., "Dioctyl phthalate, and antibacterial compound from the marine brown alga—*Sargassum wightii*", Journal of Applied Phycology, 7: 185-186 (1995).
Torane, Rasika C., et al., "Isolation and Characterisation of 1, 2 Benzenedicarboxylic acid, bis (2 ethylhexyl) ester—Dioctyl Phthalate, a Bioactive Compound from Ehretia laevis", Journal of Pharm. Research (2012) 5(6), 3251-3252.
Unknown Author, "Dioctyl Phthtalate", XP-002728241, Jun. 3, 2013, retrieved from the Internet: UURL: https://chemicalland21.com/industrialchem/plasticizer/DOP.htm, 3 pages.
Written Opinion of the International Searching Authority for PCT/IB2014/061953 mailed Sep. 24, 2014, 9 pages.
Xu, Leilei, et al., "Carbon dioxide reforming of methane over ordered mesoporous NiO—MgO—Al2O3 composite oxides", Applied Catalysis B: Environmental 108-109 (2011) p. 177-190.
"Acrylic Acid and Derivatives"; Kirk Othmer Encyclopedia of Chemical Technology; 2003, vol. 1; p. 342-369.
"Acrylic Acid", Chemsystems PERP program, PERP 08/09, Nexant, 2010, 7 pages.
Chinese Patent No. 101269899; Date of Publication: Sep. 24, 2008; Abstract Only; 1 page.
Chinese Patent No. 101367720; Date of Publication: Feb. 18, 2009; Abstract Only; 1 page.
Huang, G. et al., "Isobaric Vapor-Liquid Equilibrium for Binary Systems of Toluene + Acrylic Acid, Toluene + Acetic Acid, and Cyclohexane + Acrylic Acid at 20 kPa"; J.Chem.Eng. Data, 2011, vol. 56, pp. 3914-3919.
Japanese Patent No. 3832868; Date of Publication: Oct. 11, 2006; Abstract Only; 1 page.
Japanese Patent No. 3937495; Date of Publication: Jun. 27, 2007; Abstract Only; 1 page.
Japanese Patent No. S4946942; Date of Publication: Dec. 12, 1974; English Translation, 5 pages.
Japanese Patent No. 2005179352; Date of Publication: Jul. 7, 2005; Abstract Only; 1 page.
Japanese Patent No. 2005232008; Date of Publication: Sep. 2, 2005; English Translation, 5 pages.
Japanese Patent No. 2006316066; Date of Publication: Nov. 24, 2006; Abstract Only; 2 pages.
Japanese Patent No. S46020372; Date of Publication: Jun. 8, 1971; Machine Translation, 8 pages.
Japanese Patent No. 4809532; Date of Publication: Nov. 9, 2011; Machine Translation, 13 pages.
Japanese Patent No. H0341051; Date of Publication: Feb. 21, 1991; Abstract Only; 1 page.
Japanese Patent No. H05246941; Date of Publication: Sep. 24, 1993; Abstract Only; 2 pages.
Japanese Patent No. H09151158; Date of Publication: Jun. 10, 1997; Machine Translation, 18 pages.
Japanese Patent No. H0948744; Date of Publication: Feb. 18, 1997; Abstract Only; 1 page.
Japanese Patent No. H10306052; Date of Publication: Nov. 17, 1998; Abstract Only; 1 page.
Japanese Patent No. S4634692; Date of Publication: Oct. 11, 1971; Machine Translation, 10 pages.
Japanese Patent No. S497216; Date of Publication: Jan. 22, 1974; Machine Translation, 6 pages.
Japanese Patent No. S4995918; Date of Publication: Sep. 11, 1974; Machine Translation, 7 pages.
Japanese Patent No. S5011364; Date of Publication: Apr. 30, 1975; Machine Translation, 6 pages.

\* cited by examiner

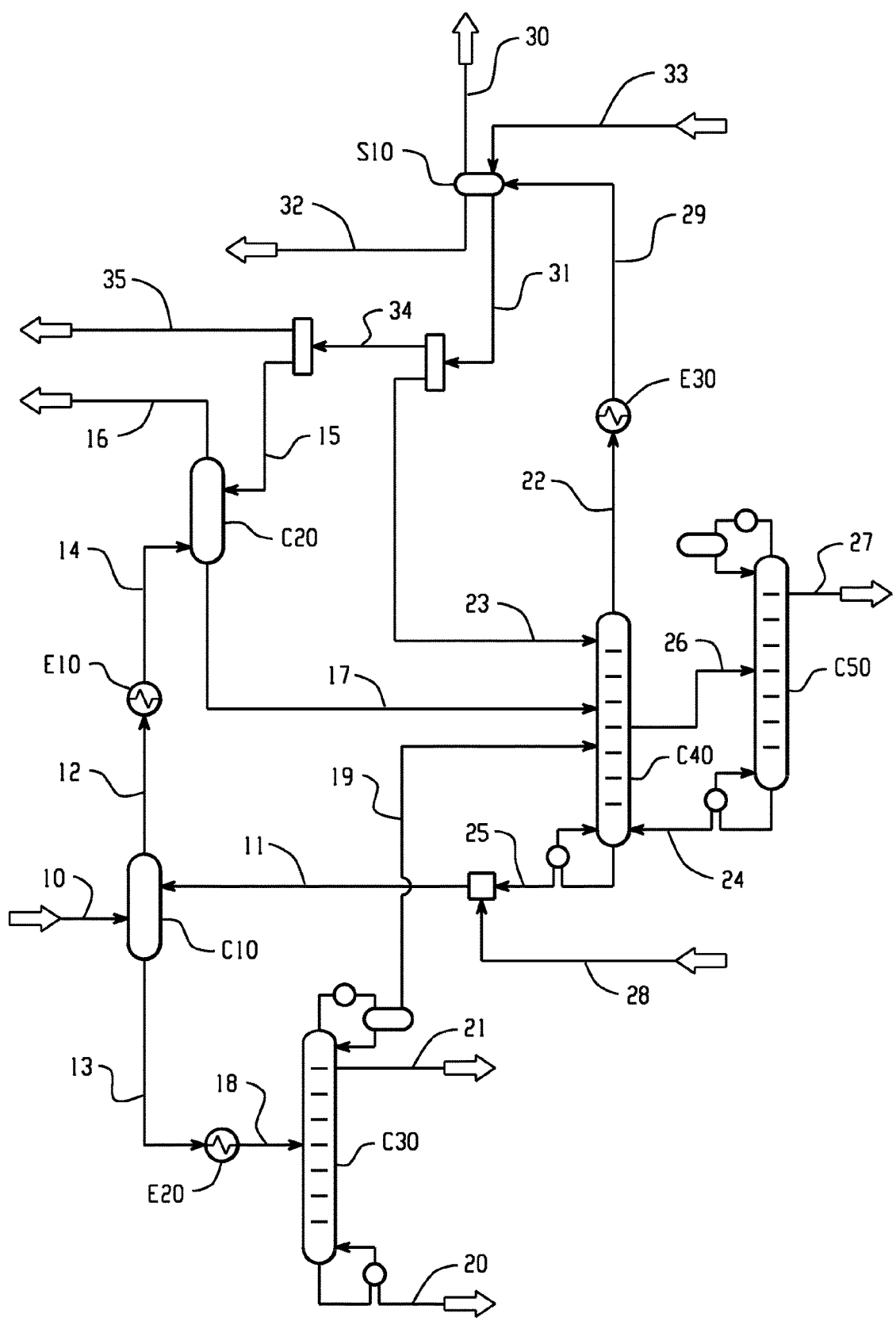

METHOD FOR THE PURIFICATION OF ACETIC ACID AND ACRYLIC ACID

CROSS-REFERENCE TO RELATED APPLICATION

This application is a national stage application of PCT/US2014/038573, filed May 19, 2014, which claims priority to U.S. Provisional Application Ser. No. 61/825,205 filed May 20, 2013, which are both hereby incorporated by reference in their entirety.

BACKGROUND

The partial oxidation of propane and propylene to organic acids, such as acrylic acid and acetic acid, is a commercially important manufacturing process. Recently improved oxidation methods produce mixtures of acrylic acid together with significant amounts of acetic acid. There is a need in the art to purify the crude reaction product.

SUMMARY OF THE INVENTION

In accordance with the purpose(s) of the invention, as embodied and broadly described herein, the invention, in an aspect, relates to an integrated scheme for purification of acetic acid and acrylic acid present in a crude product mixture, and a method for the manufacture of acrylate monomers, or specialty acrylates, from the purified acrylic acid.

Disclosed is a method for purifying an acid, wherein the method comprises:
a) producing a crude product mixture by a partial oxidation reaction, wherein the crude product mixture comprises acrylic acid and acetic acid;
b) purifying the crude product mixture by distillation using a high-boiling solvent to purify the acrylic acid; and
c) purifying the crude product mixture by distillation using a low-boiling solvent to purify the acetic acid.

While aspects of this invention can be described and claimed in a particular statutory class, such as the system statutory class, this is for convenience only and one of skill in the art will understand that each aspect of this invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DESCRIPTION OF THE FIGURE

The accompanying FIGURE, which is incorporated in and constitute a part of this specification, illustrate several aspects and together with the description serve to explain the principles of the invention.

FIG. 1 shows an overall schematic diagram of the integrated process for an aspect of the present invention for purifying mixtures of acetic acid and acrylic acid.

Additional advantages of the invention will be set forth in part in the description which follows, and in part will be obvious from the description, or can be learned by practice of the invention. The advantages will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

The term "stable," as used herein, refers to compounds that are not substantially altered when subjected to conditions to allow for their production, detection, and, in certain aspects, their recovery, purification, and use for one or more of the purposes disclosed herein.

The term "high-boiling solvent" refers to a solvent capable of dissolving acetic acid and acrylic acid, with a boiling point greater than the dew point of the gaseous stream containing these acids, i.e., in most cases, when the bulk of the gaseous stream contains water, the boiling point of the high boiling solvent is greater than about 105° C.

The term "low-boiling solvent" refers to a solvent capable of performing as an entrainer and capable of breaking the acetic acid-water azeotrope, and having a boiling point sufficiently lower than that of acetic acid so that the separation of acetic acid from the solvent can be achieved.

The terms "specialty acrylate" or "specialty acrylates" refers to esters of acrylic acid that have potential value as marketable specialty chemicals or monomers. Examples include 2-ethylhexyl acrylate.

The term "crude product mixture" refers to a product mixture that is the output of a reactor that has not been subjected to any substantial purification steps.

The term "partial oxidation reaction" refers to a reaction of a hydrocarbon with oxygen, generally in the presence of catalyst, which produces oxidation products such as alcohols, aldehydes, and carboxylic acids or mixtures thereof, with lesser amounts of complete oxidation products, i.e., $CO_2$ and $H_2O$.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

The following abbreviation is used herein: "d/s" means "downstream."

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

A. Overview

In accordance with the present invention, disclosed herein is a method for purifying an acid, wherein the method comprises:

a) producing a crude product mixture by a partial oxidation reaction, wherein the crude product mixture comprises acrylic acid and acetic acid;

b) purifying the crude product mixture by distillation using a high-boiling solvent to purify the acrylic acid; and c) purifying the crude product mixture by distillation using a low-boiling solvent to purify the acetic acid.

An efficient method for the separation and purification of both of these two acid products on an industrial scale from this crude oxidation product mixture represents a commercially significant process, and a process which is integrated with later processing steps that produces useful products such as acrylates.

B. Partial Oxidation Reaction

In an aspect, the starting materials comprise propane or propylene, or a mixture thereof.

In an aspect, the invention comprises a method for producing a crude product mixture by a partial oxidation reaction, wherein the crude product mixture comprises acrylic acid and acetic acid. In a further aspect, the crude product mixture can be produced by the partial oxidation reaction of propane by oxygen over a mixed metal catalyst. In a still further aspect, the oxidation can be carried out using conventional techniques in a reactor, which typically results in an output of a heated crude product stream with temperatures ranging from about 250° C. to about 350° C., including exemplary values of 260° C., 270° C., 280° C., 290° C., 300° C., 310° C., 320° C., 330° C., and 340° C. In further aspects, the temperature can be in a range derived from any two exemplary values. For example, the temperature can range from 260° C. to 340° C. In yet a further aspect, the crude product stream can be then directly introduced into the process as disclosed herein.

In an aspect, the partial oxidation reaction refers to a reaction where the complete oxidation of propane, for example a burning reaction of the propane, is avoided. In an aspect, a process for the partial oxidation of propane is recited, for example, in U.S. Pat. No. 5,198,580 and U.S. Pat. No. 6,160,162; all of which are hereby incorporated in its entirety for the specific purpose of disclosing a process for the partial oxidation of propane.

In a further aspect, the mixed metal catalyst comprises Mo—V—Ga—Pd—Nb—X, where X is La, Te, Ge, Zn, Si, In or W. The mixed metal catalyst can be prepared using conventional catalyst preparation techniques.

In a further aspect, the products of the partial oxidation reaction comprise propene, acrylic acid, acetic acid, or $CO_x$, where $x$ can be 1 or 2, or a mixture thereof.

In an aspect, the crude product mixture comprises acrylic acid in an amount ranging from 1 wt % to 99 wt %, based on the total weight of the crude product mixture, including exemplary values of 2 wt %, 4 wt %, 6 wt %, 10 wt %, 13 wt %, 15 wt %, 17 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 96 wt %, 97 wt %, and 98 wt %. In a further aspect, the amount can be in a range derived from any two exemplary values. For example, the crude product mixture comprises acrylic acid in an amount ranging from 2 wt % to 99 wt %, based on the total weight of the crude product mixture.

In an aspect, the crude product mixture comprises acetic acid in an amount ranging from 1 wt % to 99 wt %, based on the total weight of the crude product mixture, including exemplary values of 2 wt %, 4 wt %, 6 wt %, 10 wt %, 13 wt %, 15 wt %, 17 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 96 wt %, 97 wt %, and 98 wt %. In a further aspect, the amount can be in a range derived from any two exemplary values. For example, the crude product mixture comprises acetic acid in an amount ranging from 2 wt % to 99 wt %, based on the total weight of the crude product mixture.

In another aspect, the crude product mixture can optionally comprise a balance amount of one or more additive materials, with the proviso that the additives are selected so as to not significantly adversely affect the desired properties of the crude product mixture. Combinations of additives can be used. Such additives can be mixed at a suitable time during the mixing of the components for forming the composition. Exemplary and non-limiting examples of additive materials that can be present in the disclosed crude product mixture include an antioxidant, a stabilizer (including for example a thermal stabilizer, a hydrolytic stabilizer, or a light stabilizer), UV absorbing additive, plasticizer, lubricant, mold release agent, acid scavenger, antistatic agent, or colorant (e.g., pigment and/or dye), or any combination thereof.

The purification steps are directed to separating the acrylic acid from the crude product and separating the acetic acid from the crude product.

C. Separation and Purification of Acrylic Acid

In an aspect, the invention comprises a method for purifying the crude product mixture by distillation using a high-boiling solvent to purify the acrylic acid.

In an aspect, the crude product mixture is maintained at a temperature in the range of about 115° C. to about 125° C., including exemplary values of 116° C., 117° C., 118° C., 119° C., 120° C., 121° C., 122° C., 123° C., and 124° C. In further aspects, the temperature can be in a range derived from any two exemplary values. In a still further aspect, the crude product mixture is maintained at a temperature in the range of about 115° C. to about 120° C. In yet a further aspect, the crude product mixture is maintained at a temperature of about 120° C.

In an aspect, the invention further comprises cooling the crude product mixture. In a still further aspect, the cooling can be accomplished by an intermediate and/or intermittent cooler. In yet a further aspect, cooling can be accomplished by contacting the crude product mixture with the high-boiling solvent, which is of a lower temperature. In another aspect, the contacting can comprise the use of a quench tower.

In a further aspect, the high-boiling solvent can be described by one or more of the following properties
 a) a boiling point sufficiently above the dew point of the gaseous product stream;
 b) a low affinity for water;
 c) reactivity with the purified organic acids in downstream processing to produce valuable products such as acrylates, under a set of operating conditions that are different from conditions used to purify and separate the organic acids;
 d) low tendency to break the azeotrope normally formed between acetic acid and water in the downstream distillation column, e.g., in the column where the dehydration of organic acids is performed
 e) low tendency to form peroxides, even in the presence of introduced oxygen.

In an aspect, the high-boiling solvent can have a boiling point at least 5° C., or at least 20° C., or at least 30° C. above the dew point of the gaseous product stream, for example 10 to 80° C. or 20 to 80° C. above the dew point of the gaseous product stream at the pressure of distillation.

In a further aspect, the high-boiling solvent is not an ether, e.g., not diisopropyl ether, or a ketone, e.g. not methyl isobutyl ketone, or other solvent known to form unstable or explosive compounds.

In a further aspect, the high-boiling solvent comprises an alcohol. In a still further aspect, the high-boiling solvent comprises a linear alcohol. In yet a further aspect, the high-boiling solvent comprises hexanol, heptanol or octanol, or a mixture thereof.

In a further aspect, the high-boiling solvent comprises a branched alcohol. In a still further aspect, the high-boiling solvent comprises 2-ethyl hexanol, 2-propyl heptanol, isononanol, isoamyl alcohol, iso-bornyl alcohol, or cyclohexanol, or a mixture thereof.

In a further aspect, the high-boiling solvent comprises a polyhydric alcohol. In a still further aspect, the high-boiling solvent comprises ethylene glycol, 1,3-propane diol, 1,3-butane diol, 1,2-butane diol, 2,3-butane diol, 1,4-butane diol, 1,5-pentane diol, 1,8-octane diol, or 1-9 nonane diol, or a mixture thereof.

In a further aspect, the high-boiling solvent comprises an amino alcohol. In an aspect, the high-boiling solvent comprises 2-dimethyl aminoethanol, or 2-diethyl aminoethanol, or a mixture thereof.

In a further aspect, the high-boiling solvent is present in a molar ratio from about 2:1 to about 1:2 (solvent to acrylic acid), for example, 56 mol % of 2-ethyl hexanol and about 43 mol % of acrylic acid, with up to about 1 mol % impurities.

In a further aspect, the high-boiling solvent can comprise a minimal amount of water. In a still further aspect, a minimal amount of water is less than 10 wt %, based on the total weight of the high-boiling solvent. In yet a further aspect, a minimal amount of water is less than 5 wt %, based on the total weight of the high-boiling solvent. In a further aspect, the amount of water ranges from 0 wt % to 10 wt %, based on the total weight of the high-boiling solvent, including exemplary values of 1 wt %, 2 wt %, 3 wt %, 4 wt %, 5 wt %, 6 wt %, 7 wt %, 8 wt %, and 9 wt %. In further aspects, the amount of water can be in a range derived from any two exemplary values. For example, the amount of water can range from 0 wt % to 3 wt %, based on the total weight of the high-boiling solvent. In an aspect, the high-boiling solvent can comprise a minimal amount of water in the quench column. The quench column can typically only absorb or take up low amounts of water due to its low affinity of water.

In an aspect, the invention further comprises introducing the solvent-acid mixture into a dehydration column at a temperature from about 100° C. to about 120° C., including exemplary values of 101° C., 102° C., 103° C., 104° C., 105°

C., 106° C., 107° C., 108° C., 109° C., 110° C., 111° C., 112° C., 113 ° C., 114° C., 115° C., 116° C., 117° C., 118° C., and 119° C. In further aspects, the temperature can be in a range derived from any two exemplary values. For example, the solvent-acid mixture can be introduced into a dehydration column at a temperature from about 105° C. to about 115° C.

In a further aspect, the solvent-acid mixture is introduced into a dehydration column at a pressure from about 2 bar to 4 bar. In a still further aspect, the solvent-acid mixture is introduced into a dehydration column at a pressure of about 3 bar.

In an aspect, the method comprises continuous distillation. In another aspect, the distillation column uses trays in an amount ranging from 40 to 80 theoretical trays, including exemplary values of 41, 42, 43, 44, 45, 46, 47, 48, 50, 51, 52, 53, 54, 55, 56, 57, 58, 59, 60, 61, 62, 63, 64, 65, 66, 67, 68, 69, 70, 71, 72, 73, 74, 75, 76, 77, 78, and 79. In an aspect, the trays can be in a range derived from any two exemplary values. For example, the distillation column can use trays in an amount ranging from 50 to 70 theoretical trays.

In a further aspect, the acrylic acid is obtained with a purity ranging from about 85% to about 99%. In a still further aspect, the acrylic acid is obtained with a purity ranging from about 90% to about 99%. In yet a further aspect, the acrylic acid is obtained with a purity ranging from about 95% to about 99%. In an even further aspect, the acrylic acid is obtained with a purity of about 99%.

In an aspect, the method further comprises the addition of an inhibitor. In another aspect, the method comprises adding an inhibitor to the crude product mixture after the formation of the crude product mixture. In a further aspect, the inhibitor is added after producing the crude product mixture, but prior to a distillation step. In an even further aspect, the method comprises adding the inhibitor to the distillation column. In a yet further aspect, the method does not comprise adding an inhibitor prior to the formation of the crude product mixture.

In a further aspect, the inhibitor acts to prevent acid polymerization.

In a further aspect, the inhibitor comprises a phenolic derivative. In a still further aspect, the inhibitor comprises hydroquinone, or ethers of hydroquinone, or a mixture thereof.

In a further aspect, the inhibitor comprises a phenothiazine derivative. In a still further aspect, the inhibitor comprises quinone, or benzoquinone, or a mixture thereof.

In a further aspect, the inhibitor comprises a metal thiocarbamate. In a still further aspect, the inhibitor comprises copper dibutyldithiocarbamate, copper diethyldithiocarbamate, or copper salicylate, or a mixture thereof.

In a further aspect, the inhibitor comprises an amine. In a still further aspect, the inhibitor comprises a hydroxylamine or a phenyldiamine, or a mixture thereof.

In an aspect, the invention uses the appropriate amount of inhibitor to prevent polymerization. In a further aspect, the method comprises inhibitor in the amount ranging from 0.05 wt % to 0.5 wt %, based on the weight of the crude product mixture, including exemplary values of 0.07 wt %, 0.1 wt %, 0.2 wt %, 0.3 wt %, and 0.4 wt %. In a further aspect, the amount can be in a range derived from any two exemplary values. For example, the method can comprise an inhibitor in the amount ranging from 0.1 wt % to 0.4 wt %, based on the weight of the crude product mixture.

In another aspect, the method comprises an inhibitor in an amount ranging from 10 ppm to 500 ppm, including exemplary values of 25 ppm, 50 ppm, 75 ppm, 100 ppm, 125 ppm, 150 ppm, 200 ppm, 250 ppm, 300 ppm, 350 ppm, 400 ppm, and 450 ppm. In a further aspect, the amount can be in a range derived from any two exemplary values. For example, the method can comprise an inhibitor in an amount ranging from 25 ppm to 400 ppm.

In an aspect, the invention further comprises the addition of oxygen. For example, the purification can be conducted in the presence of the atmosphere, an oxygen-enriched atmosphere, or with oxygen bubbled into a liquid stream, for example the crude reaction product.

In a further aspect, oxygen promotes inhibitor activation. In an aspect, the oxygen promotes the activity of the inhibitor comprising a phenolic derivative or the phenothiazine derivative or a mixture thereof.

D. Separation and Purification of Acetic Acid

In an aspect, the invention comprises a method for purifying the crude product mixture by distillation using a low-boiling solvent to purify the acetic acid.

In a further aspect, the overhead vapor stream is introduced into a counter-current packed absorption column at a temperature from about 30° C. to about 50° C., including exemplary values 32° C., 34° C., 36° C., 38° C., 40° C., 42° C., 44° C., 46° C., and 48° C. In further aspects, the temperature can be in a range derived from any two exemplary values. In a still further aspect, the overhead vapor stream is introduced at a temperature from about 35° C. to about 45° C. In yet a further aspect, the overhead vapor stream is introduced at a temperature of about 40° C.

In a further aspect, the overhead vapor stream is introduced into a counter-packed absorption column at a pressure from about 2 to 4 bar. In a still further aspect, the overhead vapor stream is introduced at a pressure of about 3 bar.

In an aspect, a low-boiling solvent can be described by one or more of the following properties:
  a) has a higher affinity for organic acids than water;
  b) has the ability to wash the gases from the quench column in order to reduce the slip of organic acids down to about $1 \times 10^{-06}$ mole %;
  c) has the ability to act as an entrainer in a heteroazeotropic distillation operation; and/or
  d) the difference in boiling point between the low-boiling solvent and acetic acid, for example, is significant enough to allow acetic acid to reach concentrations of greater than about 80% on some trays within the azeotropic distillation column.

In an aspect, a difference in boiling point between the low-boiling solvent and acetic acid is at least 5° C., or at least 10° C., or at least 20° C., or at least 30° C., for example 10 to 80° C. or 20 to 80° C. at the pressure of distillation.

In a further aspect, the low-boiling solvent comprises isopropyl acetate, or water, or a mixture thereof. In a still further aspect, the low-boiling solvent comprises isopropyl acetate. Other low-boiling solvents are methyl isobutyl ketone, methyl-ethyl ketone, diisopropyl ether, dipropyl ether, di-tert-butyl ether, tert-amyl methyl ether, or ethyl acetate or a mixture thereof.

In an aspect, the crude product mixture is maintained at a temperature from about 45° C. to about 70° C., including exemplary values of 47° C., 49° C., 51° C., 53° C., 55° C., 57° C., 59° C., 61° C., 63° C., 65° C., 67° C., and 69° C. In further aspects, the temperature can be in a range derived from any two exemplary values. For example, the crude product mixture is maintained at a temperature from about 50° C. to about 60° C. In a still further aspect, the crude product mixture is maintained at a temperature from about 55° C. to about 58° C. In yet a further aspect, the crude product mixture is maintained at a temperature of about 57° C.

In a further aspect, the crude product mixture is routed through an overhead condenser to a decanter.

In a further aspect, phase splitting occurs at a temperature from about 15° C. to about 45° C., including exemplary values of 16° C., 17 ° C., 18° C., 19° C., 20° C., 21° C., 22° C., 23° C., 24° C., 25° C., 27° C., 29° C., 31° C., 33° C., 35° C., 37° C., 39° C., 40° C., 41° C., 42° C., 43° C., and 44° C. In a further aspect, the temperature can be in a range derived from any two exemplary values. In a still further aspect, phase splitting occurs at a temperature from about 20° C. to about 23° C. In yet a further aspect, phase splitting occurs at a temperature of about 22° C.

In a further aspect, the method further comprises a side draw from the hetero azeotropic distillation column routed to a purification column to obtain glacial acetic acid. In a further aspect, the method further comprises a side draw from the hetero azeotropic distillation column routed to a distillation column.

In an aspect, acetic acid is able to reach concentrations from about 50 wt % to about 90 wt %, based on the crude product mixture, in some of the column trays, including exemplary values of 55 wt %, 60 wt %, 65 wt %, 70 wt %, 75 wt %, 80 wt %, and 85 wt %. In further aspects, the weight percentage can be in a range derived from any two exemplary values. In a further aspect, acetic acid is able to reach concentrations from about 60 wt % to about 90 wt % in some of the column trays, based on the crude product mixture. In a still further aspect, acetic acid is able to reach concentrations from about 70 wt % to about 90 wt %, based on the crude product mixture, in some of the column trays. In yet a further aspect, acetic acid is able to reach concentrations from about 75 wt % to about 85 wt % in some of the column trays. In an even further aspect, acetic acid is able to reach concentrations of about 80 wt %, based on the crude product mixture, in some of the column trays.

In an aspect, acetic acid is able to reach purities from about 70 wt % to 100 wt %, including exemplary values of 75 wt %, 80 wt %, 85 wt %, 90 wt %, 95 wt %, and 99 wt %. In another aspect, the weight percentage can be in a range derived from any two exemplary values. In a still further aspect, acetic acid is able to reach purities from about 80 wt % to about 100 wt %. In yet a further aspect, acetic acid is able to reach purities from about 90 wt % to about 100 wt %. In an even further aspect, acetic acid is able to reach purities from about 95 wt % to about 100 wt %. In a still further aspect, acetic acid is able to reach purities of about 99 wt %.

In an aspect, the invention further comprises addition of an inhibitor to prevent acid polymerization.

In a further aspect, the inhibitor comprises a phenolic derivative. In a still further aspect, the inhibitor comprises hydroquinone, or ethers of hydroquinone, or a mixture thereof.

In a further aspect, the inhibitor comprises a phenothiazine derivative. In a still further aspect, the inhibitor comprises quinone, or benzoquinone, or a mixture thereof.

In a further aspect, the inhibitor comprises a metal thiocarbamate. In a still further aspect, the inhibitor comprises copper dibutyldithiocarbamate, copper diethyldithiocarbamate, or copper salicylate, or a mixture thereof.

In a further aspect, the inhibitor comprises an amine. In a still further aspect, the inhibitor comprises a hydroxylamine, or a phenyldiamine, or a mixture thereof.

In an aspect, the invention further comprises the addition of oxygen for inhibitor activation.

E. Method of Producing Acrylates from Acrylic Acid and High-Boiling Solvent

In an aspect, the invention comprises a reaction of acrylic acid with the high-boiling solvent to afford an esterification product.

In a further aspect, the high-boiling solvent is not an ether, e.g. diisopropyl ether, or a ketone, e.g. methyl isobutyl ketone, or other solvent known to form unstable or explosive compounds.

In a further aspect, the high-boiling solvent comprises an alcohol. In a still further aspect, the high-boiling solvent comprises a linear alcohol. In yet a further aspect, the high-boiling solvent comprises hexanol, heptanol or octanol, or a mixture thereof.

In a further aspect, the high-boiling solvent comprises a branched alcohol. In a still further aspect, the high-boiling solvent comprises 2-ethyl hexanol.

In a further aspect, the high-boiling solvent comprises a polyhydric alcohol. In a still further aspect, the high-boiling solvent comprises ethylene glycol, 1,3-propane diol, or 1,4-butane diol, or a mixture thereof.

In a further aspect, the high-boiling solvent comprises an amino alcohol. In another aspect, the high-boiling solvent comprises 2-dimethyl aminoethanol or 2-diethyl aminoethanol, or a mixture thereof.

In a further aspect, esterification reaction conditions include the addition of a strong acid. In a still further aspect, esterification reaction conditions include the addition of sulfuric acid, p-toulenesulfonic acid, vinyl acidic polymers, or other acidic compounds known in the art to catalyze esterifications of alcohols and acids.

In a further aspect, esterification reaction conditions include the addition of a strong acid in an amount ranging from about 0.1 wt % to 25 wt %, based on the total weight of the reagents, including exemplary values of 0.4 wt %, 0.6 wt %, 1 wt %, 2 wt %, 4 wt %, 6 wt %, 8 wt %, 10 wt %, 12 wt %, 14 wt %, 16 wt %, 18 wt %, 20 wt %, 22 wt %, and 24 wt %. In an aspect, the amount can be in a range derived from any two exemplary values. For example, the esterification reaction conditions can include the addition of a strong acid in an amount ranging from 1 wt % to 24 wt %, based on the total weight of the reagents.

In an aspect, the esterification product can be used in industry. In another aspect, the ester can be used as a fragrance, pharmaceutical composition, a poison, a monomer for polymer synthesis, a flavorant, a perfume, and/or plasticizer.

In another aspect, the esterification product comprises an acrylate.

In an aspect, the esterification product has a purity ranging from 75 wt % to 99.9 wt %, including exemplary values of 77 wt %, 79 wt %, 81 wt %, 83 wt %, 85 wt %, 87 wt %, 89 wt %, 90 wt %, 91 wt %, 93 wt %, 94 wt %, 95 wt %, 96 wt %, 97 wt %, 98 wt %, 99 wt %, and 99.5 wt %. In a further aspect, the purity can be in a range derived from any two exemplary values. For example, the esterification product can have a purity ranging from 90 wt % to 99.9 wt %.

In a further aspect, the acrylate formed can be isolated by selecting the appropriate fraction from the esterification column using standard techniques.

In a further aspect, unreacted acrylic acid and the high-boiling solvent can be recovered. In a still further aspect, unreacted acrylic acid and the high-boiling solvent can be recycled.

An aspect of the invention is shown in FIG. 1. In FIG. 1, gaseous stream 10 comes from the acrylic acid reactor after cooling. The acrylic acid reactor, not shown in the FIGURE, is based on catalytic propane oxidation. The acrylic acid reactor can also be based on conventional catalytic propylene oxidation. Stream 10 can be at about 120° C. and 3 Bar pressure and can contain acetic acid, acrylic acid, unreacted propane, and/or oxygen. Stream 10 can also contains byproducts like water, ethane, propylene, butanes, and a small amount of miscellaneous impurities which can include propionic acid, formic acid, acetone, acetaldehyde, acrolein, and/or furfural. Stream 10 can be fed to the bottom of the absorption column C10. Absorption column C10 can be a packed column and/or a tray column design. Liquid stream 11 can be rich in 2-ethylhexanol and at about 95° C., can be fed at the top of the column C10. Stream 10 and stream 11 can flow counter currently in the column and can come in contact over the packing surface and/or the trays. The liquid stream 11 flowing down in the column C10 can selectively absorb more than 95% of the incoming acrylic acid. This liquid stream 11 also can absorb other components but in significantly lower fractions. Liquid stream 13 can leave from the bottom of the column C10 at about 120° C. and can be cooled to about 50° C. in the heat exchanger E20. A cold liquid stream 18 from heat exchanger E20 can be fed to the distillation column C30. The distillation column C30 can operate under vacuum and can be designed to maximize the separation of acrylic acid and 2-ethylhexanol at the bottom of the column. Liquid stream 20 can be drawn from bottom of the column C30. The stream 20 can contain acrylic acid, 2-ethylhexanol, and/or small impurities. This stream 20 can be sent to 2-ethylhexyl acrylate production and/or acrylic acid separation. Acrylic acid and/or 2-ethylhexanol can be separated using conventional distillation technique. Recovered and purified 2-ethylhexanol can be recycled back as stream 28 along with some portion of 2-ethylhexanol. A small distillate stream 21 can be drawn from the top of the column C30 which can mainly contain acetic acid, acrylic acid, and/or water. This stream 21 can be subjected to further separation of the acids by conventional distillation and/or by crystallization. Vapor stream 19 drawn from top of the column C30 can be fed to distillation column C40. Stream 19 can mainly contain acetic acid, acrylic acid, propane, and/or water vapors.

Vapor stream 12 from the top of the column C10 can be cooled from about 121° C. to about 40° C. in the heat exchanger E10. The cooled stream 14 from E10 can be fed to the bottom of the absorption column C20. Liquid stream 15 can be at about 22° C. and rich in isopropyl acetate. Liquid stream 15 can be fed at the top of the column C20. Stream 14 and stream 15 can come in contact counter currently in the column C20 which can be filled with packing and/or trays. Column C20 can operate at about 2 Bar pressure. Acetic acid, acrylic acid, and/or 2-ethylhexanol carried in stream 14 can be absorbed in the liquid steam flowing down in the column C20 and leaves as stream 17 from the bottom of the column. The stream 17 at about 32° C. can be fed to the distillation column C40. The vapor stream 16 can leave from the top of the column C20 at about 30° C. Stream 16 can mainly contain propane, isopropyl acetate, and/or some non-condensable gases like propylene, $CO_2$, CO, and/or oxygen. Stream 16 can be sent for further processing for isopropyl acetate, propane, and/or propylene recovery. Propane and/or propylene can be sent back to acrylic acid reactor.

Distillation column C40 can operate at about 1 Bar pressure and can be designed to separate 2-ethylhexanol, isopropyl acetate, and/or acetic acid. Liquid stream 25 can be drawn from bottom of column C40 at about 157° C. Stream 25 can mainly contain 2-ethylhexanol with a concentration of more than 91% on weight basis. Stream 25 can be further mixed with stream 28 and form a stream 11. Both streams 28 and 11 are described earlier. Vapor stream 22 can be drawn from top of the column C40 which can be rich in isopropyl acetate with a concentration of more than 84% on weight basis. Stream 22 can be cooled in the heat exchanger E30 to a temperature of about 22° C. The cooled stream 29 from heat exchanger E30 can be fed to a three phase separator S10. The isopropyl acetate solvent stream 33 can also be fed into S10. The organic phase can be separated from S10 as stream 31 which can be rich in isopropyl acetate with a concentration of more than 91% on weight basis. Stream 31 can be divided into two streams: stream 23 and stream 34. Stream 23 can be used as a reflux for distillation column C40. Stream 23 can be about 79% of the stream 31. The distillate stream can be further divided into two streams: stream 15 and stream 35. Stream 15 can be about 67% of stream 34 which can be fed to column C20. Stream 35 can be sent for isopropyl acetate recovery. The vapor stream 30 from S10 can be combined with stream 16 for further treatment. Aqueous stream 32 from S10 can be sent for stripping and recovery of organics and/or the water can be sent for waste water treatment.

Stream 26 can be drawn as a side stream from distillation column C40. Stream 26 can have an acetic acid concentration of about 86% on weight basis. Stream 26 can be fed to distillation column C50 for acetic acid purification. Pure acetic acid can be recovered as distillate from the top of the column as stream 27 with a purity of more than 99.5% on weight basis. Distillation column C50 can be operated at about 2 Bar pressure. Stream 24 can be drawn from the bottom of C50 and fed back to the bottom of distillation column C40.

Any requirements of pump or compressor for the transfer of fluid from one equipment to other have not been shown in the flow scheme in FIG. 1 for simplification.

F. Aspects of the Disclosed Methods

Aspects of the present invention disclose one or more methods for the purification of acetic acid and acrylic acid from a crude product mixture. The product mixture can result, for example, from the partial oxidation reaction of propane over a mixed metal catalyst.

The invention includes at least the following aspects:

Aspect 1: A method for purifying an acid, wherein the method comprises:
  a) producing a crude product mixture by a partial oxidation reaction, wherein the crude product mixture comprises acrylic acid and acetic acid;
  b) purifying the crude product mixture by distillation using a high-boiling solvent to purify the acrylic acid; and
  c) purifying the crude product mixture by distillation using a low-boiling solvent to purify the acetic acid.

Aspect 2: The method according to aspect 1, further comprising the reaction of acrylic acid with the high-boiling solvent to produce an acrylate.

Aspect 3: The method according to any of aspects 1 and 2, further comprising an inhibitor to prevent acid polymerization.

Aspect 4: The method according to aspect 3, wherein the inhibitor comprises a phenolic derivative.

Aspect 5: The method according to aspect 3, wherein the inhibitor comprises hydroquinone, or ethers of hydroquinone, or a mixture thereof.

Aspect 6: The method according to aspect 3, wherein the inhibitor comprises a phenothiazine derivative.

Aspect 7: The method according to aspect 3, wherein the inhibitor comprises quinone, or benzoquinone, or a mixture thereof.

Aspect 8: The method according to aspect 3, wherein the inhibitor comprises a metal thiocarbamate.

Aspect 9: The method according to aspect 3, wherein the inhibitor comprises copper dibutyldithiocarbamate, copper diethyldithiocarbamate, or copper salicylate, or a mixture thereof.

Aspect 10: The method according to aspect 3, wherein the inhibitor comprises an amine.

Aspect 11: The method according to aspect 3, wherein the inhibitor comprises a hydroxylamine, or a phenyldiamine, or a mixture thereof.

Aspect 12: The method according to any of aspects 1-11, further comprising the addition of oxygen for inhibitor activation.

Aspect 13: The method according to any of aspects 1-12, wherein the high-boiling solvent comprises an alcohol.

Aspect 14: The method according to any of aspects 1-12, wherein the high-boiling solvent comprises a linear alcohol.

Aspect 15: The method according to any of aspects 1-12, wherein the high-boiling solvent comprises hexanol, heptanol or octanol, or a mixture thereof.

Aspect 16: The method according to any of aspects 1-12, wherein the high-boiling solvent comprises a branched alcohol.

Aspect 17: The method according to any of aspects 1-12, wherein the high-boiling solvent comprises 2-ethyl hexanol.

Aspect 18: The method according to any of aspects 1-12, wherein the high-boiling solvent comprises a polyhydric alcohol.

Aspect 19: The method according to any of aspects 1-12, wherein the high-boiling solvent comprises ethylene glycol, 1,3-propane diol, or 1,4-butane diol, or a mixture thereof.

Aspect 20: The method according to any of aspects 1-12, wherein the high-boiling solvent comprises an amino alcohol.

Aspect 21: The method according to any of aspects 1-12, wherein the high-boiling solvent comprises 2-dimethyl aminoethanol, or 2-diethyl aminoethanol, or a mixture thereof.

Aspect 22: The method according to any of aspects 1-21, wherein the low-boiling solvent comprises isopropyl acetate, or water, or a mixture thereof.

Aspect 23: The method according to any of aspects 1-22, wherein the partial oxidation reaction comprises propane as the starting material and a Mo—V—Ga—Pd—Nb—X mixed metal catalyst, wherein X is La, Te, Ge, Zn, Si, In or W Aspect 24: The method according to any of aspects 1-23, wherein the method further comprises the high-boiling solvent reacting downstream of the acrylic acid purification with the acrylic acid to form a specialty acrylate.

Aspect 25: The method according to any of aspects 1-24, wherein the crude product mixture further comprises water.

Aspect 26: The method according to any of aspects 1-25, wherein the method comprises at least two separate distillation steps.

G. Experimental

The following examples are put forth so as to provide those of ordinary skill in the art with a complete disclosure and description of how the compositions, articles, devices and/or methods claimed herein are made and evaluated, and are intended to be purely exemplary of the invention and not intended to limit the scope of what the inventors regard as their invention. Efforts have been made to ensure accuracy with respect to numbers, such as, for example, amounts, temperature, etcetera, but some errors and deviations should be accounted for. Unless indicated otherwise, parts are parts by weight, temperature is in ° C. or is at ambient temperature, and pressure is at or near atmospheric. Several methods for preparing the compounds of this invention are illustrated herein. Starting materials and the requisite intermediates are in some cases commercially available, or can be prepared according to literature procedures or as illustrated herein.

The following general methods of the present invention were used. The methods are provided herein to illustrate the invention, and should not be construed as limiting the invention in any way.

Table 1 is included as a prophetic example to show the mass balance in FIG. 1. Table 1 was prepared using Aspen Plus V7.3.

TABLE 1

| | MASS BALANCE, KG/H | | | | | | | | | |
|---|---|---|---|---|---|---|---|---|---|---|
| | Stream Number | | | | | | | | | |
| | 10 | 16 | 20 | 21 | 27 | 28 | 30 | 32 | 33 | 35 |
| Acetic Acid | 5191 | 36 | 5 | 1677 | 2990 | 0 | 0 | 310 | 0 | 172 |
| Acrylic Acid | 28310 | 0 | 27935 | 365 | 10 | 0 | 0 | 0 | 0 | 0 |
| Water | 27496 | 1388 | 0 | 1335 | 0 | 0 | 15 | 23939 | 0 | 819 |
| CO2 + CO | 20209 | 20089 | 0 | 0 | 0 | 0 | 95 | 3 | 0 | 23 |
| Ethane + Butanes | 1626 | 1597 | 0 | 0 | 0 | 0 | 13 | 0 | 0 | 16 |
| Oxygen | 1153 | 1151 | 0 | 0 | 0 | 0 | 2 | 0 | 0 | 0 |
| Propane | 200161 | 197262 | 0 | 0 | 0 | 0 | 1767 | 32 | 0 | 1101 |
| Propylene | 2814 | 2771 | 0 | 0 | 0 | 0 | 24 | 0 | 0 | 18 |
| 2-Ethyl Hexanol | 0 | 0 | 109990 | 0 | 0 | 110000 | 0 | 0 | 0 | 0 |
| Isopropyl Acetate | 0 | 14839 | 0 | 0 | 0 | 0 | 171 | 605 | 40853 | 25240 |
| Impurities | 2473 | 1018 | 1071 | 5 | 0 | 0 | 16 | 102 | 0 | 262 |
| Total | 289432 | 240151 | 139001 | 3383 | 3000 | 110000 | 2103 | 24991 | 40853 | 27650 |

What is claimed is:

1. A method for purifying an acid, wherein the method comprises:
   a) producing a crude product mixture by a partial oxidation reaction, wherein the crude product mixture comprises acrylic acid and acetic acid;
   b) contacting the crude product mixture with a high-boiling solvent to provide a high-boiling solvent containing acrylic acid, and a vapor stream containing acetic acid;
   c) purifying the acrylic acid by distillation using the high-boiling solvent containing acrylic acid;
   d) introducing the vapor stream containing acetic acid and a low-boiling solvent into a counter-current packed absorption column to absorb the acetic acid in the low-boiling solvent; and
   e) purifying the acetic acid by separate distillation step using the low-boiling solvent absorbing acetic acid;
   wherein the high-boiling solvent has a boiling point greater than 105° C.,
   wherein the low-boiling solvent has a boiling point lower than acetic acid.

2. The method according to claim 1, further comprising reacting the acrylic acid with the high-boiling solvent to produce an acrylate.

3. The method according to claim 1, further comprising purifying the crude product mixture in the presence of an inhibitor to prevent acid polymerization.

4. The method according to claim 3, wherein the inhibitor comprises a phenolic derivative.

5. The method according to claim 3, wherein the inhibitor comprises hydroquinone, or an ether of hydroquinone, or a mixture thereof.

6. The method according to claim 3, wherein the inhibitor comprises a phenothiazine derivative.

7. The method according to claim 3, wherein the inhibitor comprises quinone, or benzoquinone, or a mixture thereof.

8. The method according to claim 3, wherein the inhibitor comprises a metal thiocarbamate.

9. The method according to claim 3, wherein the inhibitor comprises copper dibutyldithiocarbamate, or copper diethyldithiocarbamate, or copper salicylate, or a mixture thereof.

10. The method according to claim 3, wherein the inhibitor comprises an amine.

11. The method according to claim 3, wherein the inhibitor comprises a hydroxylamine, or a phenyldiamine, or a mixture thereof.

12. The method according to claim 1, further comprising the addition of oxygen for inhibitor activation.

13. The method according to claim 1, wherein the high-boiling solvent comprises an alcohol.

14. The method according to claim 1, wherein the high-boiling solvent comprises a linear alcohol.

15. The method according to claim 1, wherein the high-boiling solvent comprises hexanol, or heptanol, or octanol, or a mixture thereof.

16. The method according to claim 1, wherein the high-boiling solvent comprises a branched alcohol.

17. The method according to claim 1, wherein the high-boiling solvent comprises 2-ethyl hexanol.

18. The method according to claim 1, wherein the high-boiling solvent comprises a polyhydric alcohol.

19. The method according to claim 1, wherein the high-boiling solvent comprises ethylene glycol, or 1,3-propane diol, or 1,4-butane diol, or a mixture thereof.

20. The method according to claim 1, wherein the high-boiling solvent comprises an amino alcohol.

21. The method according to claim 1, wherein the high-boiling solvent comprises 2-dimethyl aminoethanol, or 2-diethyl aminoethanol, or a mixture thereof.

22. The method according to claim 1, wherein the low-boiling solvent comprises isopropyl acetate, or water, or a mixture thereof.

23. The method according to claim 1, wherein the partial oxidation reaction comprises propane as the starting material and a Mo-V-Ga-Pd-Nb-X mixed metal catalyst wherein X is La, Te, Ge, Zn, Si, In or W.

24. The method according to claim 1, wherein the method further comprises the high-boiling solvent reacting downstream of the acrylic acid purification with the acrylic acid to form an acrylate.

25. The method according to claim 1, wherein the crude product mixture further comprises water.

* * * * *